United States Patent [19]

Broitman et al.

[11] Patent Number: 5,257,630
[45] Date of Patent: Nov. 2, 1993

[54] PRESSURE SENSING PROBE WITH CALIBRATION CAPABILITY

[75] Inventors: Harold Broitman, Princeton; Arthur Goldberg, Morris Plains, both of N.J.; Michael Higgins, Mission Viejo; James Mottola, Chino Hills, both of Calif.

[73] Assignees: Thermometrics, Inc.; Baxter International Inc.

[21] Appl. No.: 883,554

[22] Filed: May 15, 1992

[51] Int. Cl.[5] .......................................... A61B 5/0215
[52] U.S. Cl. ...................................... 128/675; 338/42; 73/726
[58] Field of Search ............... 128/672, 673, 675, 748; 73/706, 726, 727; 338/4, 5, 36, 42, 47

[56] References Cited

U.S. PATENT DOCUMENTS

| | | | |
|---|---|---|---|
| 3,703,099 | 11/1972 | Rouse | 73/727 |
| 3,946,724 | 3/1976 | La Balme | 73/706 |
| 4,103,555 | 8/1978 | Forster | 73/706 |
| 4,274,423 | 6/1981 | Mizuno et al. | 128/675 |
| 4,385,636 | 5/1983 | Cosman | 128/748 |
| 4,554,927 | 11/1985 | Fussell | 128/670 |
| 4,572,204 | 2/1986 | Stephens | 128/673 |
| 4,593,703 | 6/1986 | Cosman | 128/675 |
| 4,610,256 | 9/1986 | Wallace | 128/675 |
| 4,658,829 | 4/1987 | Wallace | 128/673 |
| 4,672,974 | 6/1987 | Lee | 128/673 |
| 4,712,566 | 12/1987 | Hok | 128/748 |
| 4,763,649 | 8/1988 | Merrick | 128/675 |
| 4,854,326 | 8/1989 | Merrick | 128/670 |
| 4,856,340 | 8/1989 | Garrison | 73/715 |
| 4,873,986 | 10/1989 | Wallace | 128/673 |
| 4,886,070 | 12/1989 | Demarest | 128/675 |
| 4,901,735 | 2/1990 | von Berg | 128/748 |
| 4,936,310 | 6/1990 | Engstrom et al. | 128/673 |
| 5,029,479 | 7/1991 | Bryan | 73/721 |

OTHER PUBLICATIONS

Gobiet et al, Experience With An Intracranial Pressure Transducer Readjustable In Vivo, Technical Note, J. Neurosurgery, vol. 39, pp. 272-276 (Feb. 1974).
Goldberg, Arthur, Novel Temperature and Pressure Sensors: Changes in Technologies and Products, Advances in Critical Care Technologies Conference, Boston, May 16, 1991.
Sones, William, Fax Transmission from William Sones, President of Medical Measurements, Inc. to Arthur Goldberg, May 25, 1992.

*Primary Examiner*—Lee S. Cohen
*Assistant Examiner*—Marianne Parker
*Attorney, Agent, or Firm*—Lerner, David, Littenberg, Krumholz & Mentlik

[57] ABSTRACT

A biomedical pressure sensor having a pressure sensing diaphragm is provided with a distensible membrane overlying the diaphragm, and the diaphragm is provided with one or more holes. During normal operation, externally applied pressure forces the membrane against the diaphragm so that the membrane and diaphragm deform under pressure as a unit and transmit pressure-applied forces to a force transducer within the probe housing. When a reference pressure exceeding the externally applied pressure is supplied within the probe housing, such reference pressure passes through the hole in the diaphragm and forces the membrane away from the diaphragm, thereby isolating the diaphragm from the externally applied pressure and bringing the diaphragm to a zero-differential pressure condition. Use of a hole in the diaphragm permits an extremely compact construction.

12 Claims, 1 Drawing Sheet

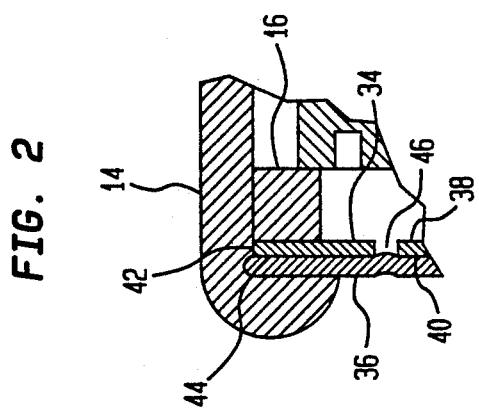
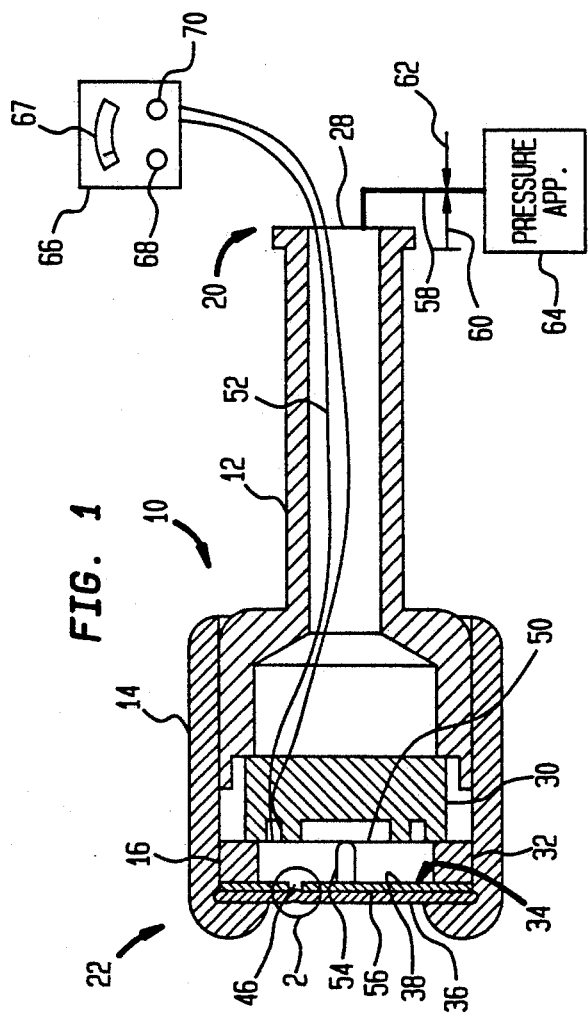
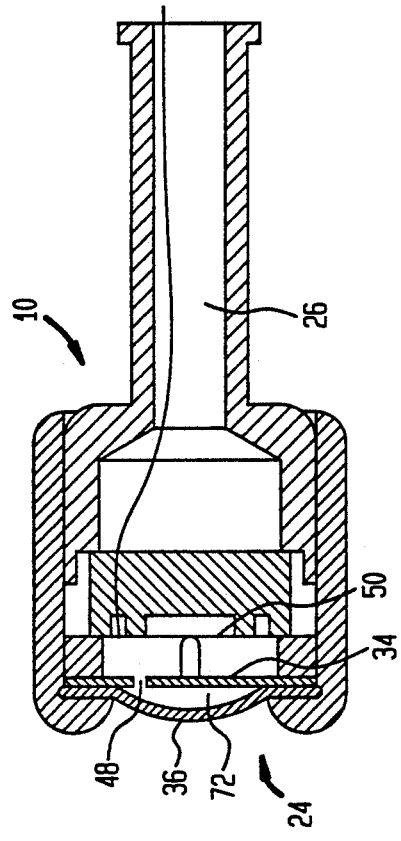

PRESSURE SENSING PROBE WITH CALIBRATION CAPABILITY

FIELD OF THE INVENTION

The present invention relates to pressure-sensing probes.

BACKGROUND OF THE INVENTION

Pressure-sensing probes are utilized in numerous biomedical and physiological monitoring procedures for measuring pressures prevailing in the body of a subject. Two principal types of pressure monitoring devices are commonly utilized in the biomedical arts. The so-called "extracorporeal" type utilizes a transducer positioned outside of the patient's body and connected to the region of interest by a hollow catheter or the like. The pressure from the area of interest is transmitted by a column of fluid. This approach has significant disadvantages including generally poor response to dynamic, rapidly changing pressures at the tip of the catheter and the practical difficulties associated with maintaining an open, unclogged lumen within the patient's body.

In another approach, commonly referred to as a "intracorporeal" or "in situ" sensing approach, a pressure transducer is physically inserted into the body so that the transducer itself is disposed within the region of interest for direct monitoring of the pressure therein. Typically, the pressure transducer is mounted on an elongated body such as a catheter at the distal end thereof. The pressure transducer typically is connected by wires or other appropriate signal-transmitting means to the proximal end of the probe, i.e., the end of the probe structure which is positioned outside of the subject's body during use. Because the pressure is measured directly at the region of interest, without an intervening fluid column, many of the difficulties associated with extracorporeal pressure sensing are eliminated. However, a pressure transducer for placement within the patient's body ordinarily must be very small. For example, a transducer for insertion through an intravascular catheter typically should be less than about 2.3 mm wide. Moreover, such a transducer should be safe, accurate and manufacturable at reasonable cost. All these requirements taken together pose a formidable engineering challenge.

A desirable transducer for intracorporeal pressure sensing is set forth in commonly assigned U.S. Pat. No. 4,554,927. As set forth in the '927 patent, the pressure transducer may incorporate a piezoresistive beam element positioned inside of a housing adjacent an opening in the housing. An imperforate flexible diaphragm extends across the opening. A plate may be mounted on the interior surface of the flexible diaphragm. Pressure applied on the diaphragm would be transmitted to the plate and hence to the beam element. Accordingly, the beam element would be subjected to a load directly related to the difference between external pressure surrounding the exterior of the housing and a reference pressure inside of the housing. The beam element will provide an electrical resistance directly related to this force and hence directly related to the pressure differential. As further set forth in the '927 patent, this beam element may be formed in conjunction with another element as a unitary, U-shaped element. The second element provides a resistance which varies with temperature and allows compensation for temperature effects on the first-said beam element.

As set forth in commonly assigned U.S. Pat. No. 4,886,070, the flexible diaphragm desirably applies a preload to the sensor. That is, when the external pressure equals the internal pressure, tension in the diaphragm itself desirably applies a force to the force transducer. Such preload is desirable to assure that the diaphragm is effectively linked to the transducer element during normal conditions of use.

Apart from temperature compensation, there is still need to calibrate the sensor and the electronic signal-processing devices used to monitor the signal from the sensor. Typically, the signal processing equipment has both "gain" and "zero" settings. The zero setting adjusts the system to display a reading corresponding to a predetermined baseline value, typically zero, when the probe is surrounded by a predetermined deform pressure, typically atmospheric pressure. Where the reference and datum pressures are both atmospheric pressure, then the datum pressure condition corresponds to a condition of zero differential pressure applied at the transducer, i.e., a condition where the pressure outside and inside the probe housing are the same. The gain setting controls the amount by which the displayed pressure value will change for a given change in the actual pressure surrounding the probe. Both the zero and gain settings ordinarily must be adjusted to correct values for an individual instrument and for an individual electronic signal process system. Moreover, it is often necessary to readjust these settings to compensate for changes in the signal processing equipment, the probe or both during the course of a medical procedure. For example, it may be necessary to readjust these values if the signal processing equipment is momentarily disconnected during the course of a procedure, or if the signal processing equipment is changed and new equipment is substituted. It is difficult to adjust the zero setting of the system while an intracorporeal pressure sensor is in place within the patient. The sensor is exposed to the varying pressure prevailing in the patient's body, and hence cannot be placed under the datum pressure.

Considerable effort has been devoted by the art heretofore towards a solution to this problem. Thus, as shown in U.S. Pat. No. 4,936,310 and 4,712,566, a moveable valve device may be provided for isolating the transducer from the surroundings so that the transducer may be subjected to datum pressure for zero setting purposes. These arrangements add size and complexity to the system. The aforementioned U.S. Pat. No. 4,886,070 discloses a method for achieving calibration, including zero setting, while the probe remains in place. In this method, the interior or reference pressure inside of the pressure sensor is varied in a systematic manner and changes in the displayed readings are observed. One reference point used in this process is the pressure required to overcome the preload applied by diaphragm and also overcome the external pressure prevailing in the vicinity of the pressure sensor. Although this method can achieve accurate calibration while the pressure sensor remains in place, still further simplification would be desirable. Thus, it would be desirable if the user could, through a simple procedure, bring the sensor to a condition where the sensor will provide the same output as it would provide under the reference or datum conditions.

One approach which has been employed heretofore is to surround the entire distal tip of the probe structure with a flexible balloon. In normal use the pressure within the patient's body surrounding the distal tip is exerted on the pressure sensor through the balloon. For example, Gobiet et al, Experience With An Intracranial Pressure Transducer Readjustable In Vivo, Technical Note, J. Neurosurgery, Volume 39, pp. 272-276 (February, 1974) discloses a pressure sensing probe having a diaphragm-equipped pressure transducer at the distal end of the probe structure. The probe structure has interior or reference space at the distal end connected to a port or source of reference pressure through a first lumen. A balloon surrounds the entire distal end of the sensor body, the balloon being connected to another pressure source through a separate second lumen. During normal operation, atmospheric pressure is applied through both lumens. The fluid pressure surrounding the distal tip, being greater than atmospheric pressure forces the balloon inwardly against the diaphragm so that the pressure transducer is subjected to a differential pressure corresponding to the difference between the fluid pressure and the atmospheric pressure prevailing inside the reference space. When an arbitrary pressure greater than the surrounding fluid pressure is applied through both lumen simultaneously, the balloon is inflated and hence stands away from the pressure transducer, thereby isolating the transducer from the surroundings within the patient. Because the pressure inside the reference space is the same as the pressure applied within the balloon, there is zero differential pressure across the diaphragm. The pressure transducer "sees" a zero differential pressure, exactly the same condition as would prevail if the distal tip were exposed to atmospheric pressure while the reference pressure was also atmospheric. Therefore, the zero setting of the signal processing system can be adjusted in this condition.

Van Berg, U.S. Pat. No. 4,901,735 discloses another, similar diaphragm-type pressure transducer which uses only a single lumen for connection of the reference and balloon pressures. Thus, in the '735 patent device, the diaphragm is mounted in a housing at the distal end of the device, the housing having several ports remote from the diaphragm itself leading to the exterior surface of the housing. The entire housing, including the various ports, is encased by the balloon. When a reference pressure applied through the single lumen connected to this housing exceeds the surrounding pressure, the balloon is inflated and pushed away from the diaphragm, thereby placing the diaphragm-type pressure transducer under a zero-differential pressure condition and permitting zero-setting. When the reference pressure applied through this single lumen is less than the surrounding pressure, the balloon collapses and the diaphragm is again exposed to the differential pressure. Both of these approaches impart considerable size and complexity to the pressure sensor, particularly at the distal tip of the sensor body. U.S. Pat. No. 3,703,099 discloses other, similar devices. Although the principal disclosure in the '099 patent is directed to pressure transducers other than diaphragm-type transducers, the '099 patent does mention that one could use a diaphragm-type transducer with the distensible membrane or balloon system and with "fluid access means", not further defined, for both sides of the diaphragm.

Despite all of this effort in the prior art however, there is still need for further improvement. In particular, there is a need for a device which would combine the accurate and convenient zero-setting capabilities of the isolation balloon or membrane-type devices with the compactness and the other desirable attributes of diaphragm-type pressure sensors such as those shown in the '927 and '070 patents.

SUMMARY OF THE INVENTION

The present invention addresses these needs.

One aspect of the present invention provides a pressure sensing probe including a housing having a sensing port open to the outside of the housing and an interior space extending to the sensing port. The probe also includes means for providing a reference pressure in the interior space. For example, where the probe housing is elongated and has proximal and distal ends, the sensing port may be disposed adjacent the distal end of the housing. The means for providing a reference posture may include a reference pressure port disposed adjacent to proximal end communicating with the interior space as, for example, by a lumen extending lengthwise through the body. The probe most desirably also includes a flexible diaphragm having a central portion, a periphery surrounding said central portion and oppositely directed inside and outside surfaces. The diaphragm desirably is mounted in the sensing port so that the diaphragm extends substantially across the sensing port. The periphery of the diaphragm is connected to the housing but the central portion of the diaphragm is moveable with respect to the housing upon flexure of the diaphragm. The inside surface of the diaphragm faces into the interior space whereas the outside surface of the diaphragm faces toward the outside of the housing. The diaphragm most preferably has a hole extending through it between its interior and exterior surfaces. This hole desirably is of relatively small diameter as compared for example to the overall dimensions of the diaphragm.

The probe desirably also includes force transducer means for providing a signal representing inwardly directed forces on the central portion of the diaphragm, i.e., forces applied to the central portion of the diaphragm directed toward the interior space. Additionally, the probe includes a flexible membrane sealingly mounted to the housing and extending across the sensing port outside of the diaphragm. Most preferably, the flexible membrane is sealed to the housing immediately around the periphery of the sensing port. The membrane may be normally slack, so that when an exterior pressure outside of the housing at the sensing port exceeds the reference pressure within the interior space, the membrane will bulge inwardly against the diaphragm, and the diaphragm will engage and support the membrane against inward movement. In this condition, the membrane effectively "bridges" across the hole in the diaphragm. Thus, a force directly related to the excess of the exterior pressure over the reference pressure inside the interior space will be applied to the diaphragm through the membrane. This force will be transmitted by the diaphragm to the force transducer means and represented in the signal provided by the force transducer means.

The membrane is also free to bulge outwardly away from the diaphragm when the reference pressure inside the interior space exceeds the exterior pressure surrounding the outside of the housing at the sensing port. In this condition, the reference pressure is transmitted through the hole in the diaphragm. This reference pressure thus forces the membrane outwardly, away from the diaphragm.

Thus, in normal operation, when the reference pressure is less than the exterior pressure around the outside of the body structure, the membrane and the diaphragm effectively act as a single, imperforate diaphragm. In this condition, the hole in the diaphragm has essentially no effect, inasmuch as it is plugged by the membrane. However, when the reference pressure is increased above the exterior pressure, the outwardly bulging membrane effectively isolates the diaphragm from the exterior pressure. In this condition, the pressure on both side of the diaphragm is the same. Accordingly, any force exerted by the diaphragm on the force transducer means is of precisely the same magnitude as would be exerted by the diaphragm on the force transducer means under conditions of equal reference pressure and exterior pressure.

Preferred probes according to this aspect of the present invention therefore can provide essentially all of the benefits achievable through use of an inflatable membrane or balloon, while still retaining a structure which is essentially as compact and as simple as a diaphragm-type pressure transducer using an imperforate diaphragm without such a membrane or balloon feature. The ability to combine zero-setting capability with a compact, rugged structure provides a unique combination of benefits.

These and other objects, features and advantages of the present invention will be more readily apparent from the detailed description of the preferred embodiment set forth below, taken in conjunction with the accompanying drawings.

BRIEF DESCRIPTION OF THE DRAWINGS

FIG. 1 is a diagrammatic sectional view depicting a probe in accordance with one embodiment of the invention.

FIG. 2 is a fragmentary sectional view on an enlarged scale depicting the area indicated in FIG. 1.

FIG. 3 is a sectional view similar to FIG. 1 but depicting the probe of FIG. 1 in a different condition of operation.

DETAILED DESCRIPTION OF THE PREFERRED EMBODIMENTS

The probe illustrated in FIG. 1 has a housing 10 including a tubular body element 12, collar 14. A ring-like interior support piece 16 and a further interior support piece 18 are also incorporated in the structure of housing 10. The housing has a proximal end 20 and a distal end 22, and defines a sensing port 24 at the distal end and a reference pressure port 28 at the proximal end. The components of housing 10 are illustrated as separately formed, assembled pieces. However, it should be clearly understood that some or all of these may be formed as a unitary body, or, conversely, that additional, separate pieces may be incorporated in the housing. The separate components of the housing are fixedly mounted to one another, i.e., they will not move relative to one another during normal use of the device, although the same may be detachable from one another for maintenance or repair purposes.

The housing defines a continuous interior space 26 extending from reference pressure port 28 at the proximal end of the body to sensing port 24 at the distal end. Interior support pieces 16 and 18 may be provided with appropriate cutouts or bores as schematically indicated at 30 and 32 to permit free fluid communication between the reference pressure port and the distal end of the interior space, immediately adjacent sensing port 24.

A thin, flexible diaphragm 34 and a flexible membrane 36 extend across sensing port 24. As best seen in FIGS. 1 and 2, diaphragm 34 has an inside surface 38 facing inwardly (toward the right in FIGS. 1 and 2) into the interior space defined by the housing 10 and an outside surface 40 (FIG. 2) facing outwardly, to the left in FIGS. 1 and 2 towards the outside of the body structure. Membrane 36 overlies the outside surface 40 of diaphragm 34. A peripheral region 42 of the diaphragm, and a peripheral region 44 of membrane 36 are engaged and held by the housing 10, these being trapped between interior support piece 16 and collar element 14 of the housing. Thus, membrane 36 is sealingly engaged, about the periphery of sensing port 24, with the housing. Diaphragm 34 has a hole 46 extending through it, between its inside surface 38 and its outside surface 40. Sensing port 24 is generally in the form of a circular aperture, i.e., the same would appear to have a circular shape if seen in elevational view looking into the sensing port, to the right in FIG. 1. The sensing port may be, for example, about 1.0 to about 1.5 mm in diameter.

Membrane 36 and diaphragm 38 are generally in the form of circular disks. These elements desirably are slightly larger in diameter than the diameter of the sensing port and hence may be about 1.6 mm to about 1.8 mm in diameter. Membrane 36 desirably is formed from a soft, rubbery, distensible material such as a rubber or other elastomer selected from the group consisting of latex, synthetic rubber and silicone rubber. Most preferably, the material of the membrane has a hardness less than about 30 Shore A durometer. Membrane 36 desirably is less than about 0.10 mm thick and most desirably between about 0.05 mm and about 0.125 mm thick. Diaphragm 34 desirably is formed from a relatively high-modulus material, i.e., a material having a tensile modulus above about $15 \times 10^6$ psi, such as titanium. However, diaphragm 34 desirably is less than about 0.011 mm thick and most desirably between about 0.005 mm and about 0.008 mm thick and hence is substantially flexible despite the high modulus of elasticity of the diaphragm material. Hole 46 desirably is less than about 0.5 mm in diameter and more desirably between about 0.25 mm and about 0.375 mm in diameter. The edges of hole 46 at least at the exterior diaphragm surface 40 facing membrane 36 may be rounded or chamfered so that only relatively dull edges face membrane 36.

A beam-like piezoresistive force transducer element 50 is supported by interior support piece 18 within the interior space, slightly proximally of diaphragm 34. Force transducer element 50 is adapted to change its electrical resistance upon application of a force, such as a bending force to it. Force transducer 50 may be formed as part of a combined force and temperature transducer element as described, for example, in U.S. Pat. No. 4,554,927. Transducer element 50 is electrically connected to leads, schematically indicated at 52, for transmission of electrical signals from the force transducer element to the proximal end 20 of the probe. Leads 52 may also carry power to the transducer element. A force transmission member 54 mechanically interconnects a central portion 56 of diaphragm 34 with transducer element 50. Element 54 may be secured to the diaphragm, to the transducer element or both. The dimensions of these components are selected so that when no differential pressure forces are applied to the diaphragm, the diaphragm is under slight tension and exerts a slight preload force on transducer element 50 through force transmission member 54.

In operation, reference port 28 at the proximal end of the housing may be connected to a source of reference pressure. For example, the entire housing structure 10 may be mounted on the end of a catheter or similar tube schematically indicated at 58 and connected through such tube to a valve 60 adapted to connect the tube, and hence the interior space 26 of body 10 either to the atmosphere through a port 62 or to a controllable pressure source 64. Leads 52 may be connected to a signal processing and display device 66 having gain and zero adjustments 70 and 68 respectively and a display means, such as a meter 67 or the like. Signal processing device 66 also provides power to the transducer element 50 through leads 52.

The system initially may be calibrated before placement in the body of a subject. Valve 60 is actuated to connect the interior space 26 to the atmospheric inlet port 62 while the device is outside of the patient's body, under normal atmospheric pressure. At this point, the zeroing control 68 of the signal processing device 66 is adjusted until the meter on the signal processing device gives a reading indicating zero pressure, i.e., zero pressure difference between the exterior pressure prevailing around the outside of housing 10 and the reference pressure within the interior space 26. Valve 60 may then be actuated to connect the interior space of the probe to pressure application device 64, which in turn may be actuated to provide a known negative pressure within the interior space 26. In this condition, the atmospheric pressure will force membrane 36 inwardly against diaphragm 34. As seen in FIG. 2, membrane 36 bridges across hole 46. The pressure exerted on the outside of the membrane acts on the membrane and the diaphragm essentially as if the membrane and diaphragm were a single structure. This pressure tends to force the central portion 56 of the diaphragm inwardly and hence forces the force transmission member 54 inwardly, towards the interior space (to the right as seen in FIG. 1). Such force increases the load applied on transducer element 50, thus causing a variation in the signal supplied along leads 52 to signal processing apparatus 66. The difference between the signal prevailing at this step and the signal prevailing under the atmospheric pressure setting step discussed above, is a change in signal representing a pressure equal in absolute value to the negative pressure applied through pressure application device 64. The gain setting control 70 of signal processing apparatus 66 is set to display a positive numeric value equal to this absolute value.

The probe may then be inserted into the patient's body and positioned in the region where a pressure is to be sensed. For example, if an arterial pressure is to be sensed, the transducer may be inserted within the patient,s artery. The interior space 26 is connected to the atmospheric pressure inlet port 62 through valve 60. In this condition, atmospheric pressure prevails within interior space 26. Provided that the pressure within the patient's body is higher than the atmospheric pressure (as will normally be the case) membrane 36 will continue to lie against diaphragm 34, substantially in the condition illustrated in FIGS. 1 and 2. Once again, the exterior pressure forces the membrane against the diaphragm and forces the membrane and diaphragm inwardly towards the transducer element substantially in the same manner as if the diaphragm were imperforate, i.e., as if hole 46 did not exist. The transducer element 50 will provide signals continually indicating the difference between the externally applied pressure and the reference pressure within space 26.

To recalibrate the pressure sensor and/or the signal processing apparatus, valve 60 is actuated to isolate the interior space from the atmospheric pressure inlet and pressure application device 64 is actuated to apply a high pressure above the prevailing pressure within the patient,s body, i.e., above the pressure surrounding the exterior of housing 10 adjacent the sensing port 24. Air within space 26 is brought to this higher pressure. In this condition, air passes through hole 48 in diaphragm 34 so that the higher pressure is applied to the inwardly facing side of membrane 36, thereby forcing the membrane 36 outwardly, away from diaphragm 34 and opening a space 72 (FIG. 3) therebetween. In this condition, diaphragm 34 is effectively isolated from the exterior environment. The pressure within the patient's body applied on the exterior of membrane 36 is not applied to the diaphragm. The pressure within space 72 is equal to the pressure within interior space 26. Accordingly, diaphragm 34 is under no differential pressure loading. Therefore, the force exerted on transducer element 50 by diaphragm 34 is exactly the same as the force exerted by the diaphragm on the transducer element in the previously mentioned zeroing step. The force is exactly the same as if atmospheric prevailed both inside and outside of body structure 10.

In this condition, the zero-setting control 68 (FIG. 1) of the signal processing apparatus is adjusted until the meter in such apparatus indicates a zero pressure condition. It is unnecessary to control the pressure applied by pressure source 64 during this recalibration zero-setting step with any particular accuracy. So long as the pressure applied in this step exceeds the prevailing pressure within the patient at the distal end of the probe, and is not so high as to rupture membrane 36, the results will be the same. For example, where the sensing port is positioned in an artery of a human subject, any pressure above the systolic blood pressure of the subject will be effective in this step. Thus, a reference pressure of about 200 to about 300 mm Hg typically will suffice.

After the zero-setting step, the gain may be adjusted, if desired, by bringing the reference pressure within interior space 26 in succession to any two values less than the pressure prevailing in the patient's body at the sensing port. The gain setting of the signal processing device so that the difference between the average pressures indicated by the signal processing device using these two different reference pressures is equal to the actual difference between such reference pressures. One of these two reference pressures may be the datum pressure, i.e, atmospheric pressure.

As will be readily appreciated, numerous variations and combinations of the feature described above can be utilized without departing from the present invention as defined by the claims. For example, the diaphragm may be provided with more than one hole. The diaphragm and membrane need not be round, disk-like elements but instead may be rectangular or of other shapes. Also, the hole or holes in the diaphragm need not have a circular shape, but instead may be formed as an elongated slot. Also, the physical orientation of the components may be altered so that the sensing port opens laterally rather than in the distal direction. The physical arrangement of the housing may be varied from the elongated shape illustrated. Alternatively, the housing may be integrated with a tubular probe, catheter or the like, so that the proximal end of the housing will be disposed outside of the patient's body when the distal end, with the sensing port and associated components is introduced within the body. Other known forms of force transducer, such as resistive strain gauge, magnetostrictive, piezoelectric or capacitive transducers can be used. Also, it is not essential that the force transducer convert the force into an electrical signal. Thus, a force transducer which converts the force into an optical signal may also be employed.

As these and other variations and combinations may be employed without departing from the present invention, the foregoing description of preferred embodiments should be taken by way of illustration rather than by way of limitation of the present invention as defined by the claims.

What is claimed is:

1. A pressure-sensing probe comprising:
   (a) a housing having a sensing port open to the outside of the housing and a interior space extending to said sensing port;
   (b) means for providing a reference pressure in said interior space;
   (c) a a flexible diaphragm, said diaphragm having a central portion and a periphery, said periphery of said diaphragm being connected to said housing around said sensing port, said central portion of said diaphragm being movable upon flexure of said diaphragm, said diaphragm having oppositely-directed inside and outside surfaces, the inside surface facing into said interior space, the outside surface facing toward the outside of said housing; said diaphragm having a hole extending through it between said inside and outside surfaces;
   (d) force transducer means for providing a signal representing inwardly-directed forces on said diaphragm; and
   (e) a flexible membrane sealingly mounted to said housing extending across said sensing port outside of said diaphragm so that when an exterior pressure outside said housing at said sensing port exceeds said reference pressure in said interior space said diaphragm can engage and support said membrane against inward movement, and a force directly related to the excess of said exterior pressure over said reference pressure will be applied to said diaphragm through said membrane and such force will be transmitted by said diaphragm to said force transducer means, said membrane being free to bulge outwardly away from said diaphragm when said reference pressure exceeds said exterior pressure, whereby said reference pressure will be applied to both said inside and outside surfaces of said diaphragm and said diaphragm and said force sensing means will be isolated from said membrane and said exterior pressure.

2. A probe as claimed in claim wherein said diaphragm extends entirely across said sensing port.

3. A probe as claimed in claim 1 wherein said force transducer means includes a force-sensing element disposed in said interior space and means for connecting the central portion of said diaphragm to said force-sensing element for transmission of inwardly-directed forces from said central portion of said diaphragm to said force-sensing element.

4. A probe as claimed in claim 3 wherein said diaphragm and said means for connecting said central portion of said diaphragm to said force-sensing element are positioned about said sensing port so that diaphragm applies a preload to said force-sensing element when equal pressures are applied on said inside and outside surfaces of said diaphragm.

5. A probe as claimed in claim 4 wherein said force-sensing element includes a beam element extending generally parallel to said inside surface of said diaphragm.

6. A probe as claimed in claim 1 wherein said diaphragm is metallic.

7. A probe as claimed in claim 1 wherein said hole is less than about 0.5 mm in diameter.

8. A probe as claimed in claim 1 or claim 7 wherein said membrane is less than about 0.10 mm thick.

9. A probe as claimed in claim 8 wherein said membrane is formed from a material selected from the group consisting of latex, synthetic rubber, and silicone rubber.

10. A probe as claimed in claim 8 wherein said membrane is formed from a soft polymeric material.

11. A probe as claimed in claim 1 wherein said membrane is secured to said housing at the periphery of said sensing port.

12. A probe as claimed in claim 1 wherein said housing is elongated and has proximal and distal ends, said sensing port being disposed adjacent said distal end, said means for providing a reference pressure including a reference pressure port disposed adjacent said proximal end and communicating with said interior space.

* * * * *